(12) United States Patent
O'Dell et al.

(10) Patent No.: US 6,282,948 B1
(45) Date of Patent: Sep. 4, 2001

(54) ROTARY VISCOMETRY WITH A LOW HEAT-TRANSMISSIBLE SPINDLE

(75) Inventors: Patrick T. O'Dell, Vassar; Gregory C. Miiller, Coleman; Theodore W. Selby, Midland; Robert H. Seer, Midland, all of MI (US)

(73) Assignee: Tannas Company, Midland, MI (US)

( * ) Notice: Subject to any disclaimer, the term of this patent is extended or adjusted under 35 U.S.C. 154(b) by 0 days.

(21) Appl. No.: 09/427,427

(22) Filed: Oct. 26, 1999

(51) Int. Cl.⁷ .............................. G01N 11/14; F25D 23/06
(52) U.S. Cl. .................. 73/54.28; 73/54.32; 73/54.35
(58) Field of Search .................. 73/54.28, 54.32, 73/54.35, 54.27, 54.02

(56) References Cited

U.S. PATENT DOCUMENTS

| | | | |
|---|---|---|---|
| 3,115,769 | * 12/1963 | Bowen, Jr. ............................. | 73/59 |
| 4,643,021 | * 2/1987 | Mattout ................................. | 73/59 |
| 5,301,541 | * 4/1994 | Joseph et al. ....................... | 73/54.32 |
| 5,349,847 | * 9/1994 | Lee et al. ............................. | 73/54.28 |
| 5,369,988 | * 12/1994 | Selby .................................. | 73/54.28 |
| 5,481,903 | * 1/1996 | King et al. .......................... | 73/54.28 |
| 5,513,517 | * 5/1996 | Van Meter et al. ................. | 73/54.28 |
| 5,526,681 | * 6/1996 | Selby .................................. | 73/54.43 |
| 5,531,102 | * 7/1996 | Brookfield et al. ................. | 73/54.32 |
| 5,587,522 | 12/1996 | Selby .................................. | 73/54.28 |
| 5,798,454 | * 8/1998 | Nakazeki et al. ................... | 73/54.28 |
| 5,874,665 | * 2/1999 | Larsson .............................. | 73/54.28 |
| 5,874,666 | * 2/1999 | Bishop ................................ | 73/54.35 |
| 6,167,752 | * 1/2001 | Raffer ................................. | 73/54.28 |

OTHER PUBLICATIONS

ASTM D 2983—87 (Reapproved 1993).
Catalog, Garolite listings. 1998.
Selby, T., U.S. patent application 08/490,111, filed Jun. 6, 1995, (abandoned), specification as filed.

* cited by examiner

*Primary Examiner*—Hezron Williams
*Assistant Examiner*—David J. Wiggins
(74) *Attorney, Agent, or Firm*—Christopher John Rudy

(57) ABSTRACT

Low heat-transmissible spindle for rotary viscometry includes an elongate, radially balanced, straight shaft made of a suitably stiff material having a low heat-transmission value, with a head monolithic with the shaft which can contact and interface with a test fluid to yield drag from the contact and interface when the spindle is rotated in the fluid; and a spindle coupling nut attached to the shaft opposite the head. For example, the shaft may be made of a woven glass fabric cylinder laminated with a synthetic resin, and the head made of stainless steel. A rotary viscometer can be equipped with the spindle, and fluid viscosity can be determined by employing the same in a rotary viscometric protocol, for example, ASTM D 2983.

10 Claims, 1 Drawing Sheet

ROTARY VISCOMETRY WITH A LOW HEAT-TRANSMISSIBLE SPINDLE

BACKGROUND TO THE INVENTION

I. Field of the Invention

The present invention concerns rotary viscometry with a low heat-transmissible spindle, as well as the spindle and associated viscometer apparatus with the spindle included therewith.

II. Prior Art and Problems

Standard test method ASTM D 2983 for low-temperature viscosity of automotive fluid lubricants measured by Brookfield viscometer determines the low-shear-rate viscosity in the temperature range from −5 to −40 degrees C. The fluid viscosity, of course, is temperature-dependent, and certain ways and means have been introduced and disclosed to assist in controlling the temperature so as to provide more reliable data. See, e.g., ASTM D 2983-87 (Reapproved 1993) and Selby, U.S. Pat. Nos. 5,526,681 and 5,587,522, which are incorporated herein by reference.

A concern for possible heat-transfer losses through the metal spindle led Theodore W. Selby to develop a spindle having a shaft bisected into upper and lower metal components and tied together by a phenolic composite sleeve. That spindle was an attempt to control a problem of transfer of heat, and it has been used since 1958. As noted by Mr. Selby in abandoned U.S. patent application Ser. No. 08/490,111, several drawbacks attend this bisected-shaft approach:

1) The spindle shaft, being separated into three parts, is subject to imbalance and undesirable, accidental disassembly.
2) The phenolic composite insulator portion of the three-part shaft is typically of a larger diameter than the metal rod portion, commonly twice or more that of the metal spindle portion, and extends for a significant distance along the axis of rotation, commonly an inch.
3) The large insulator portion requires an upper closure to the stator having a larger opening to accommodate the insulator passing through. This engenders the introduction of ambient air into the stator and test fluid, causing an unwanted rise in the temperature of the test fluid, which disturbs the accuracy of the measurement.
4) Manufacture of this item is more involved than desired. With amelioration of the same concern in mind, Mr. Selby invented a heat-dissipating viscometer rotor comprising an elongate member distributed along an axis of rotation having opposing attachment and sample-immersion ends, and a protuberance (which can be a set of fins) therebetween, all the same typically made from stainless steel, which was set forth in the abandoned '111 application.

Unfortunately, data obtained by the aforementioned ASTM protocol even as improved so well by the disclosures of the Selby patents can be less accurate than desired in today's world of high precision lubricant technology. Furthermore, as noted, data obtained with the buffered-shaft spindle was not highly accurate, and the finned rotor did not dissipate enough heat.

It would be desirable to ameliorate the problems remaining.

SUMMARY OF THE INVENTION

Through dedicated and patient research and study done in the development of the present invention, it has been confirmed or discovered that indeed a source of the problem is that heat was transferred indeed through the metal spindle during conditioning and testing under an ASTM D 2983 type protocol. This transfer of heat through the known metal spindle, and even with employment of the bisected-shaft and finned rotors, would raise the temperature of the test sample enough to affect its viscosity and introduce inaccuracies in the data. In addressing the problem, moreover, heat transfer was not the only cause of inaccurate data as it was also confirmed or discovered that, in use of the bisected-shaft spindle intended to address the problem of heat transfer by a metal spindle in the protocol, inaccurate data was generated indeed through wobble of that spindle. This wobble effect could compound any insufficient heat-transfer retardation from the short buffer segment of the heat-insulating material.

Accordingly, the present invention provides, in one aspect, a low heat-transmissible spindle for rotary viscometry comprising an elongate, radially balanced, straight shaft made of a suitably stiff material having a low heat-transmission value, a viscosity sensing section (head) monolithic with the shaft which can contact interface with a test fluid to yield drag from the contact and interface when the spindle is rotated in the fluid, and a spindle coupling nut attached to the shaft opposite the head. In other aspects, it provides a rotary viscometer equipped with such a spindle, and a method of determining fluid viscosity by employing the same in a rotary viscometric protocol.

The invention is useful in lubricant testing.

Significantly, by the invention, viscometric test data can be improved in kind. In particular, accuracy is notably increased. The spindle is structurally sound and economically manufactured.

Numerous further advantages attend the invention.

DRAWINGS IN BRIEF

The drawings form part of the specification hereof. With respect to the drawings, the following is briefly noted:

DETAILED DESCRIPTION OF ILLUSTRATIVE EMBODIMENTS OF THE INVENTION

The invention can be further understood by the present detail which may be read in view of the drawings. The same should be taken in an illustrative and not necessarily limiting sense.

Figure 1:
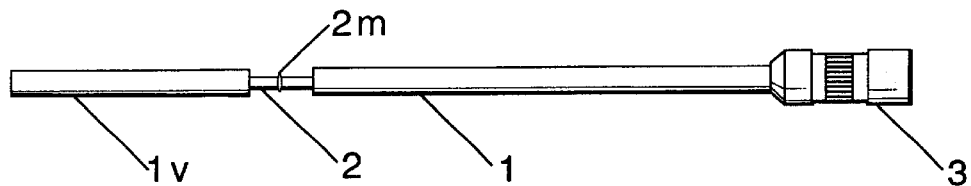
FIG. 1 is a side view showing an all metal spindle of the prior art suitable for use in the ASTM D 2983 protocol or modification thereof such as one in which a sample cell disclosed in the aforementioned Selby patents is employed.
Figure 2:
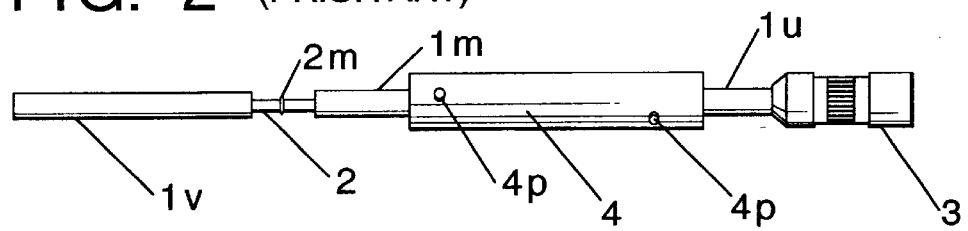
FIG. 2 is a side view showing a buffered shaft spindle of the prior art for such protocols.
Figure 3:
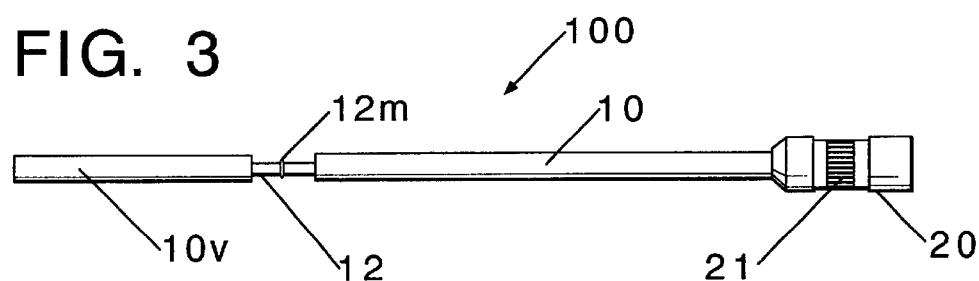
FIG. 3 is a side view showing a spindle of the present invention suitable for use in such protocols.
Figure 4:
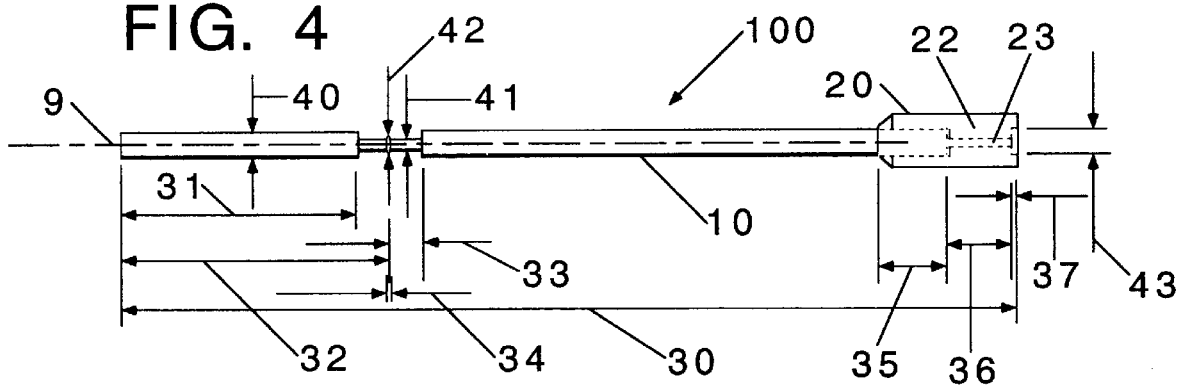
FIG. 4 is a side plan view of the spindle of FIG. 3.
Figure 5:
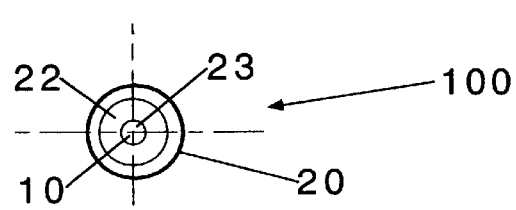
FIG. 5 is a top view of the spindle of FIGS. 3 & 4.

With respect to the drawings, FIG. 1 shows a standard, all metal spindle of the prior art having metal shaft 1 with viscosity sensor section (head) 1*v*, immersion groove 2, immersion mark 2*m*, and press-fit spindle coupling nut 3 of the same metal as the shaft, for example, stainless steel; FIG. 2 shows a buffered shaft spindle of the prior art having metal intermediate shaft portion 1*m*, upper shaft portion 1*u*, head 1*v*, immersion groove 2 with immersion mark 2*m* machined into a metal portion of the shaft, press-fit metal spindle coupling nut 3, and plastic epoxy buffer sleeve 4 which is pinned to the intermediate and upper metal shaft portions 1m, 1u by pins 4P. FIGS. 3–5 show a low heat-transmissible spindle for rotary viscometry 100 of the present invention.

With respect to the invention, the spindle 100 subsists about elongate axis of rotation 9, and has elongate, radially balanced, straight shaft 10 including viscosity sensor section (head) 10v such as, in general, of a straight, generally cylindrical rod, into which immersion groove 12 with immersion mark 12m can be provided, for example, by machining with a lathe; and spindle coupling nut 20 press-fit to a lower portion of the shaft. The shaft 10 is made of any suitably stiff material having a low heat-transmission value such as a suitable epoxy, phenolic or engineering thermoset plastic. For example, the shaft can be machined from a ⅛-inch diameter grade G-11 Garolite woven glass fabric cylinder (rod) laminated with a synthetic phenolic resin. The nut 20, for example, of stainless steel, is attached to the shaft 10, for example, by press-fitting. On the outside surface of the nut 20 there can be knurling or standard region of vertically oriented fins 21, and press-fit inside the head 20 can be countersunk standard disc 22 with threaded center hole 23, say, with 3–56 size left handed threads, useful for keeping the rod from unscrewing during operation. The spindle 100 and its components may be made to any suitable or standard size, for example, a standard number-4 size (#4 LV cylindrical spindle). As depicted in FIG. 4, the spindle 100, which is the #4 LV cylindrical spindle having its stainless steel head 20 press-fit to its G-11 Garolite composite shaft 10, can have the following dimensions:

| Feature | Dimension |
| --- | --- |
| Overall length 30 | 4.50 inches |
| Viscosity sensing head length 31 | 1.250 inches |
| Immersion mark distance 32 | 1.40 inches |
| Immersion groove half length 33 | 0.15 inches |
| Immersion mark length 34 | 0.025 inches |
| Shaft in nut length 35 | 0.250 inches |
| Inner disc length 36 | 0.250 inches |
| Upper nut countersink length 37 | 0.050 inches |
| Overall shaft diameter 40 | 0.1250 inches |
| Immersion groove diameter 41 | 0.070 inches |
| Immersion mark diameter 42 | 0.0850 inches |
| Upper nut inside wall diameter 43 | 0.17 inches. |

Thus, the overall shape and size of the spindle 100 can be similar to if not the same as the all metal spindle of FIG. 1. It can enjoy, however, a distinctive two-tone look, say, with a generally matte surfaced, yellow, yellow-green, green, green-brown, or brown composite shaft 10, for example, of the G-11 Garolite (which can have a pleasant appearing color, roughly yellow-green 152-B according to a standard R.H.S. Colour Chart) and a contrastingly shiny stainless steel nut 20. Among other advantages, the shaft 100 has a low heat transfer coefficient.

The spindle of the invention such as the spindle 100 can be attached to an otherwise standard rotary viscometer. It can be used in methods for determining fluid viscosity by employing the same in a rotary viscometric protocol, for example, the ASTM D 2983 protocol or modifications thereof employing the test stator cells of the aforementioned Selby patents. Thus, such a method can include 1) providing a rotary viscometer equipped with a low heat-transmissible spindle for rotary viscometry comprising an elongate, radially balanced, straight shaft made of a suitably stiff material having a low heat-transmission value, a viscosity sensing section (head) monolithic with the shaft which can contact and interface with a test fluid to yield drag from the contact and interface when the spindle is rotated in the fluid, and a spindle coupling nut attached to the shaft opposite the viscosity sensing section; 2) providing a stator filled with a test fluid; 3) immersing the head of the spindle in the test fluid; 4) rotating the spindle and its head; and 5) measuring drag of the head in rotary contact with the test fluid. Computer monitoring can be effected. Advantageously, the test fluid is a liquid lubricant, especially an oil, most especially a motor oil.

CONCLUSION

The present invention is thus provided. Numerous adaptations and modifications can be effected within its spirit, the literal claim scope of which is particularly pointed out as follows:

We claim:

1. A low heat-transmissible spindle for rotary viscometry comprising an elongate, radially balanced, straight shaft made of a suitably stiff material having a low heat-transmission value, a viscosity sensing section monolithic with the shaft which can contact interface with a test fluid to yield drag from the contact and interface when the spindle is rotated in the fluid; and a spindle coupling nut attached to the shaft opposite the viscosity sensing section.

2. The spindle of claim 1, which is made of a woven glass fabric cylinder laminated with a synthetic resin.

3. The spindle of claim 2, wherein the spindle coupling nut is metal.

4. A rotary viscometer equipped with a low heat-transmissible spindle for rotary viscometry comprising:

the rotary viscometer; and the low heat-transmissible spindle for rotary viscometry, which includes an elongate, radially balanced, straight shaft made of a suitably stiff material having a low heat-transmission value, a viscosity sensing section monolithic with the shaft which can contact interface with a test fluid to yield drag from the contact and interface when the spindle is rotated in the fluid; and a spindle coupling nut attached to the shaft opposite the viscosity sensing section.

5. The viscometer of claim 4, wherein the spindle is made of a woven glass fabric cylinder laminated with a synthetic resin.

6. The viscometer of claim 5, wherein the spindle coupling nut of the spindle is metal.

7. A method of determining fluid viscosity comprising providing a rotary viscometer equipped with a low heat-transmissible spindle for rotary viscometry, said spindle including an elongate, radially balanced, straight shaft made of a suitably stiff material having a low heat-transmission value, a viscosity sensing section monolithic with the shaft which can contact interface with a test fluid to yield drag from the contact and interface when the spindle is rotated in the fluid; and a spindle coupling nut attached to the shaft opposite the viscosity sensing section;

providing a stator filled with a test fluid;

immersing the viscosity sensing section of the spindle in the test fluid;

rotating the spindle and its viscosity sensing section; and measuring drag from the viscosity sensing section in rotational contact with the test fluid.

8. The method of claim 7, wherein the test fluid is a liquid lubricant.

9. The method of claim 8, wherein the lubricant is an oil.

10. The method of claim 9, wherein the oil is a motor oil.

* * * * *